(12) United States Patent
Lenzi et al.

(10) Patent No.: US 12,208,026 B2
(45) Date of Patent: Jan. 28, 2025

(54) PROSTHESIS WITH POWERED ANKLE AND TOE JOINTS

(71) Applicant: UNIVERSITY OF UTAH RESEARCH FOUNDATION, Salt Lake City, UT (US)

(72) Inventors: Tommaso Lenzi, Salt Lake City, UT (US); Lukas R. Gabert, Salt Lake City, UT (US); Minh Tran, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 18/285,146

(22) PCT Filed: Mar. 29, 2022

(86) PCT No.: PCT/US2022/022374
§ 371 (c)(1),
(2) Date: Sep. 29, 2023

(87) PCT Pub. No.: WO2022/212397
PCT Pub. Date: Oct. 6, 2022

(65) Prior Publication Data
US 2024/0180723 A1    Jun. 6, 2024

Related U.S. Application Data

(60) Provisional application No. 63/168,128, filed on Mar. 30, 2021.

(51) Int. Cl.
*A61F 2/66*    (2006.01)
*A61F 2/68*    (2006.01)
(Continued)

(52) U.S. Cl.
CPC .... *A61F 2/6607* (2013.01); *A61F 2002/5043* (2013.01); *A61F 2002/5072* (2013.01);
(Continued)

(58) Field of Classification Search
CPC ............ A61F 2/6607; A61F 2002/5043; A61F 2002/5072; A61F 2002/6621;
(Continued)

(56) References Cited

U.S. PATENT DOCUMENTS 9,579,221 B2 * 2/2017 Mosler .................... A61F 2/66
2005/0216097 A1    9/2005 Rifkin
(Continued)

FOREIGN PATENT DOCUMENTS

WO    WO-2020041491 A1 *  2/2020   ............... A61F 2/68

OTHER PUBLICATIONS

CN102885660 (Year: 2013).*
(Continued)

*Primary Examiner* — Bruce E Snow
(74) *Attorney, Agent, or Firm* — Workman Nydegger

(57) ABSTRACT

Disclosed herein is a robotic ankle foot prosthesis that replicates the key biomechanical functions of the biological ankle and toe joints while matching the weight, size, and battery life of passive microprocessor-controlled prostheses. A single actuator powers the ankle and toe joints. The mechanism maximizes the mechanical energy regeneration during walking while imitating the physiological features of energy injection by way of the ankle joint and energy dissipation by way of the toe joint.

36 Claims, 6 Drawing Sheets

(51) Int. Cl.
*A61F 2/50* (2006.01)
*A61F 2/70* (2006.01)
*A61F 2/76* (2006.01)

(52) U.S. Cl.
CPC ............... *A61F 2002/6621* (2013.01); *A61F 2002/6836* (2013.01); *A61F 2002/701* (2013.01); *A61F 2002/7635* (2013.01)

(58) Field of Classification Search
CPC ........ A61F 2002/6836; A61F 2002/701; A61F 2002/7635
See application file for complete search history.

(56) References Cited

U.S. PATENT DOCUMENTS

| | | |
|---|---|---|
| 2011/0208322 A1 | 8/2011 | Rifkin et al. |
| 2015/0230943 A1 | 8/2015 | Marlin et al. |
| 2015/0328020 A1 | 11/2015 | Clausen et al. |
| 2023/0218410 A1* | 7/2023 | Petrone ................ A61F 2/66 623/50 |

OTHER PUBLICATIONS

"Proprio Foot," Ossur, Retrieved at Https://www.ossur.com/prosthetic-solutions/products/dynamic-solutions/proprio-foot., Retrieved on Apr. 2022, pp. 14.

Adams P. F. et al., "Current estimates from the National Health Interview Survey, 1996," Natl. Heal. Surv. Vital Heal. Stat, 1999, pp. 1-203.

Au et al., "Powered ankle-foot prosthesis," IEEE Robot. Autom. Mag, vol. 15, 2008, pp. 52-59.

Au, S. K. et al., "Powered ankle-foot prosthesis improves walking metabolic economy," IEEE Trans. Robot, vol. 25, 2009, pp. 51-66.

Baimyshev, A. et al., "Design and Preliminary Assessment of Lightweight Swing-Assist Knee Prosthesis," in 2018 40th Annual International Conference of the IEEE Engineering in Medicine and Biology Society (EMBC), 2018, pp. 3198-3201.

Bellman, R. D. et al., "SPARKy 3: Design of an active robotic ankle prosthesis with two actuated degrees of freedom using regenerative kinetics," 2nd IEEE RAS EMBS Int. Conf. Biomed. Robot. Biomechatronics, 2008, pp. 511-516.

Bruening, D. A. et al., "Analysis of a kinetic multi-segment foot model part II: Kinetics and clinical implications," Gait Posture, vol. 35, 2012, pp. 535-540.

Bruening, D. A. et al., "Analysis of a kinetic multi-segment foot model. Part I: Model repeatability and kinematic validity," Gait Posture, vol. 35, 2012, pp. 529-534.

Collins, S. H. et al., "Recycling energy to restore impaired ankle function during human walking," PLoS One, vol. 5, Issue 5, 2011, e9307.

Convens, B. et al. "Modeling, Design and Test-Bench Validation of a Semi-Active Propulsive Ankle Prosthesis with a Clutched Series Elastic Actuator," IEEE Robot. Autom. Lett, vol. 4, 2019, pp. 1823-1830.

Goldfarb, M. et al., "Realizing the promise of robotic leg prostheses," Sci. Transl. Med, vol. 5, 2013, p. 210ps15.

Hahn, A. et al., "First results concerning the safety, walking, and satisfaction with an innovative, microprocessor-controlled four-axes prosthetic foot," Prosthet. Orthot Int, vol. 42, Issue 3, 2018, pp. 350-356.

Honert, E. C. et al., "Effect of toe joint stiffness and toe shape on walking biomechanics," Bioinspiration and Biomimetics, vol. 13, Issue 6, 2018.

Lawson, B. E. et al., "A Robotic Leg Prosthesis: Design, Control, and Implementation," Robot. Autom. Mag, vol. 21, 2014, pp. 70-81.

Lenzi, T. et al., "A lightweight robotic ankle prosthesis with non-backdrivable cam-based transmission," in 2017 International Conference on Rehabilitation Robotics (ICORR), 2017, pp. 1142-1147.

Lenzi, T. et al., "Design and preliminary testing of the RIC hybrid knee prosthesis," in 2015 37th Annual International Conference of the IEEE Engineering in Medicine and Biology Society (EMBC), 2015, pp. 1683-1686.

Lenzi, T. et al., "Design, development, and testing of a lightweight hybrid robotic knee prosthesis," Int. J. Rob. Res, vol. 37, 2018, pp. 953-976.

Lenzi, T. et al., "Design, Development, and Validation of a Lightweight Non-backdrivable Robotic Ankle Prosthesis," IEEE/ASME Trans. Mechatronics, 2019, pp. 1-11.

Narang, Y. et al., "The Effects of Prosthesis Inertial Properties on Prosthetic Knee Moment and Hip Energetics Required to Achieve Able-bodied Kinematics," IEEE Trans. Neural Syst. Rehabil. Eng, vol. 24, Issue 7, 2016, pp. 754-763.

Nester, C. J. et al., "Movement of the human foot in 100 pain free individuals aged 18-45: Implications for understanding normal foot function," J. Foot Ankle Res, vol. 7, 2014, pp. 1-10.

Nickel, E. et al., "Passive prosthetic ankle-foot mechanism for automatic adaptation to sloped surfaces," J. Rehabil. Res. Dev, vol. 51, 2014, pp. 803-814.

Schmalz, T. et al., "Energy expenditure and biomechanical characteristics of lower limb amputee gait: The influence of prosthetic alignment and different prosthetic components," Gait Posture, vol. 16, 2002, pp. 255-263.

Shepherd, M. K. et al., "The VSPA Foot: A Quasi-Passive Ankle-Foot Prosthesis with Continuously Variable Stiffness," IEEE Transactions on Neural Systems and Rehabilitation Engineering, vol. 25, Issue 12, 2017, pp. 2375-2386.

Sinitski E. H. et al., "Biomechanics of the ankle-foot system during stair ambulation: Implications for design of advanced ankle-foot prostheses," J. Biomech, vol. 45, 2012, pp. 588-594.

Smith, J. D. et al., "Effects of prosthetic mass distribution on metabolic costs and walking symmetry," J. Appl. Biomech, vol. 29, 2013, pp. 317-328.

Smith, J. D. et al., "Short and Longer Term Changes in Amputee Walking Patterns Due to Increased Prosthesis Inertia," JPO J. Prosthetics Orthot, vol. 23, 2011, pp. 114-123.

Takahashi, K. Z. et al., "Energy neutral: The human foot and ankle subsections combine to produce near zero net mechanical work during walking," Sci. Rep, vol. 7, 2017, pp. 1-9.

Versluys, R. et al., "Prosthetic feet: state-of-the-art review and the importance of mimicking human ankle-foot biomechanics," Disabil. Rehabil. Assist. Technol, vol. 4, 2009, pp. 65-75.

Wang, Q. et al., "Walk the walk: A lightweight active transtibial prosthesis," IEEE Robot. Autom. Mag, 2015, pp. 80-89.

Zhu, J. et al., "PANTOE 1: Biomechanical design of powered ankle-foot prosthesis with compliant joints and segmented foot," in IEEE/ASME International Conference on Advanced Intelligent Mechatronics, AIM, 2010, pp. 31-36.

Zhu, J. et al., "Pantoe II: Improved version of a powered transtibial prosthesis with ankle and toe joints," in Frontiers in Biomedical Devices, BIOMED—2018 Design of Medical Devices Conference, DMD 2018 (2018).

International Search Report and Written Opinion received for PCT Patent Application No. PCT/US2022/022374, mailed on Jun. 22, 2022, 8 pages.

\* cited by examiner

PROSTHESIS WITH POWERED ANKLE AND TOE JOINTS

CROSS-REFERENCE TO RELATED APPLICATIONS

This patent application is a nationalization of and claims priority to PCT Application No. PCT/US2022/022374 filed on Mar. 29, 2022 and titled "Prosthesis with Powered Ankle and Toe Joints," which claims priority to and the benefit of U.S. Provisional Application No. 63/168,128, filed Mar. 30, 2021 and titled "Prosthesis with Powered Ankle and Toe Joints". Each of the aforementioned applications is incorporated by reference herein in their entirety.

STATEMENT REGARDING FEDERALLY SPONSORED RESEARCH

This invention was made with government support under grant no. 1925371 awarded by the National Science Foundation and grant no. HD098154 awarded by the National Institutes of Health. The government has certain rights in the invention.

BACKGROUND

Technical Field

The present disclosure is directed to devices capable of effective implementation of a biomechanically appropriate toe joint in a robotic prosthesis.

Related Technology

Lower-limb amputation severely limits functional mobility and quality of life. Below-knee amputations are the most prevalent, representing 71% of dysvascular amputations. The simplest and most used ankle-foot prosthesis solution for individuals with below-knee amputation consists of a carbon fiber foot rigidly connected to the user's residual limb. This solution is lightweight and robust but has very limited functionality because the biomechanical function of the missing biological ankle is approximated by the carbon-fiber foot as a simple stiffness element.

More recently, ankle-foot prostheses have been developed with an ankle joint actuated by passive elements such as springs and dampers. In some advanced devices, the mechanical impedance of the ankle can be actively controlled during the gait cycle to improve ambulation. A fundamental limitation of these prosthetic technologies is that they cannot actively generate movements and inject net-positive energy into the gait cycle, which are critical functions of a biological leg. Prosthesis users compensate for these deficiencies with their residual limb and contralateral leg resulting in a slower, less efficient, and less stable gait compared to able-bodied individuals.

Other ambulation activities, such as climbing stairs and ramps or transitioning between sitting and standing are exceedingly difficult with the available passive prostheses. Thus, improved prosthesis technologies are necessary to address the unmet needs of individuals with below-knee amputations.

Despite the improvements in electrical and mechanical efficiency, available actuation solutions have significant limitations. For example, four-bar linkages are affected by the inherent tradeoff between linkage size and load. In addition, they have a limited usable range of motion (ROM).

As a result, prior ankle prostheses designed with four-bar linkages cannot fit within the foot envelope and must be placed vertically on the shank portion of the ankle-foot prosthesis, which results in a large prosthesis build height.

Parallel springs can be made relatively lightweight and small but are typically optimized for walking, which requires a stiff dorsiflexion spring with an equilibrium point close to the neutral ankle position. As a result, the ankle prosthesis cannot rest in a dorsiflexed position, negatively affecting activities of daily living such as ambulation on stairs, descending ramps, transitioning between sitting and standing, and comfortable resting dorsiflexed positions for sitting and standing.

An alternative design strategy, known as a hybrid design, aims to reduce the prosthesis size and weight by powering only a subset of activities or avoiding net-positive energy injection. This design strategy relaxes the speed and torque requirements on the actuation, resulting in smaller and lighter prostheses. However, in contrast to fully-powered prostheses, hybrid prostheses cannot assist users during all ambulation activities. Therefore, there is a tradeoff between the functionality of a powered prosthesis and the actuation size and weight.

The size and weight of a powered prosthesis affect its function and usability. The build height determines the portion of the amputee population that can use a powered prosthesis, specifically depending on the subject's height and residual limb length. In addition, the prosthesis weight affects biomechanics and clinical outcomes negatively. For example, a larger prosthesis weight has been shown to increase metabolic energy cost, exacerbate stance time and swing time asymmetries and increases hip effort during walking. Thus, a compact and lightweight fully powered prosthesis is necessary to improve ambulation for most individuals with below-knee amputation.

The biomechanical function of the toe joint is often overlooked in robotic leg prostheses. Biomechanical analysis of nonamputee gait shows that the toe joint has a substantial effect on gait kinematics during level ground walking. The toe joint has also been shown to play an important role in transferring power within the foot/ankle structure. A robotic ankle/foot prosthesis featuring a powered toe joint has been described previously. Unfortunately, the additional toe actuator results in an even bigger and heavier prosthesis.

A passive toe joint can be implemented to minimize the added weight and size. For example, a small and lightweight leaf spring has been used in a prosthesis emulator. However, this spring-actuated toe joint stores and releases energy during the gait cycle. In contrast, the biological toe joint dissipates energy during level ground walking.

Accordingly, there is an ongoing need for devices capable of effective implementation of a biomechanically appropriate toe joint in a robotic prosthesis.

SUMMARY

Disclosed herein is a robotic ankle foot prosthesis that replicates the key biomechanical functions of the biological ankle and toe joints while matching the weight, size, and battery life of passive microprocessor-controlled prostheses. In one embodiment, a single actuator powers the ankle and toe joints. The mechanism maximizes the mechanical energy regeneration during walking while imitating the physiological features of energy injection by way of the ankle joint and energy dissipation by way of the toe joint. A powered ankle-foot prosthesis with these characteristics has the potential to improve real-world mobility in individuals with lower-limb amputation.

In one embodiment, a powered assistive ankle and foot device comprises a shank assembly, a tarsal assembly, and a toe assembly. The shank assembly is mechanically connected to the tarsal assembly, and the tarsal assembly is mechanically connected to the toe assembly. The shank assembly includes a shank pivot shaft offset from and mechanically connected to an ankle joint. The toe assembly includes a toe pivot shaft offset from and mechanically connected to a toe joint. A proximal section of the tarsal assembly is mechanically connected to the shank pivot shaft a distal section of the tarsal assembly is mechanically connected to the toe pivot shaft. The tarsal assembly includes or is associated with a linear actuator. The linear actuator powers movement of both the ankle joint and the toe joint. The movement of the ankle joint and the toe joint may be simultaneous.

In some embodiments, the linear actuator is configured to adjust the distance between the shank pivot shaft and the toe pivot shaft to thereby provide simultaneous torque to both the ankle joint and the toe joint. For example, when a distance between the shank pivot shaft and the toe pivot shaft is lessened, the ankle joint may move in plantarflexion and the toe joint may move in toe flexion, whereas when a distance between the shank pivot shaft and the toe pivot shaft is increased, the ankle joint may move in dorsiflexion and the toe joint may move in toe extension.

In some embodiments, the linear actuator comprises a screw assembly (e.g., a ball screw assembly). In some embodiments, the linear actuator further comprises a compliant element (e.g., a spring) configured to move the toe joint toward a neutral position when no force is applied via the linear actuator. For example, the compliant element may be mechanically connected to the nut of the screw assembly and functions to move the nut toward a neutral position along the screw when the screw is not rotated. In some embodiments, the compliant element is attached to and spans between a proximal anchor and a distal anchor, wherein the proximal anchor is connected to the nut of the screw assembly and the distal anchor is connected to the toe pivot shaft.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Introduction & Selected Definitions

Figure 1A:
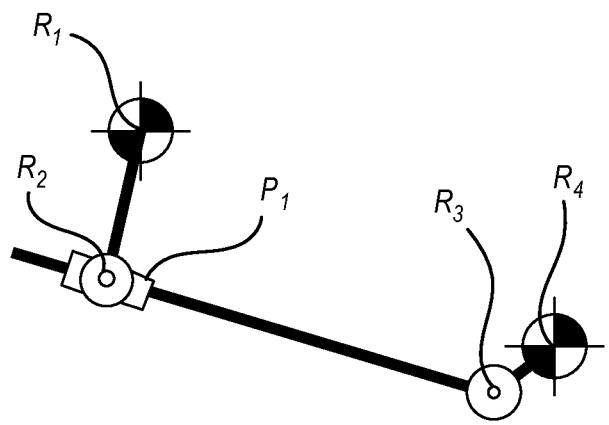
FIG. 1A illustrates a simplified view of an actuation mechanism that may be utilized to power both ankle and toe joint movement in a prosthetic device.

Example embodiments disclosed herein are described in the context of a prosthesis device. However, the scope of the invention is not so limited and extends, more generally, to assistive prostheses, orthoses, and exoskeletons (collectively referred to herein as "assistive device(s)").

Embodiments may be constructed of any suitable material(s). Structural elements and/or other elements may be constructed of metals, such as aluminum, titanium, or steel, as well as composites, carbon, carbon fiber materials, and any other materials that are relatively light and offer relatively good strength and durability. A variety of plastics may be used as well for one or more elements of embodiments of the invention.

Where two or more elements of an embodiment are rotatably connected to each other, any suitable mechanisms and elements may be employed to implement the rotatable connection. For example, pins, solid or hollow shafts, bolts, and rivets, may comprise an element of a rotatable connection. Likewise, ancillary components such as bushings, sleeves, and bearings of any suitable type, may be provided as part of one or more of the disclosed rotatable connections.

Embodiments described herein may include one or more "compliant" elements. As used herein, a compliant element is a component or group of components that physically deforms or otherwise changes physical configuration in response to an input force. Such elements can return automatically to an undeformed or relatively less deformed physical state upon reduction or cessation of the input force. To illustrate, a spring may return on its own to an undeformed (i.e., neutral) or relatively less deformed state when a deforming force previously applied to that spring is reduced or removed.

In some embodiments, a compliant element or group thereof may exhibit both elastic and viscous behaviors. Regardless of the physical configuration or arrangement of the complaint element(s), the elastic behavior may be linear or nonlinear. Similarly, the viscous behavior of a passively variable element may also be linear or nonlinear. In addition, the stiffness and damping coefficients of a compliant element may be constant or variable. Compliant elements may be made of any suitable material(s), examples of which include metal, plastic, rubber, or combinations of these. The term compliant member embraces any structure or combination of structures whose behavior, at least in an elastic range, can be characterized by an equation of the form: F=Kx (Hooke's Law), where F=applied force, K=spring constant, and x=displacement. Examples include springs, loop or belt structures, and the like.

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

Example Kinematic Mechanism

FIG. 1A illustrates a simplified view of an actuation mechanism that may be utilized to power both ankle and toe joint movement in a prosthetic device. The kinematics of the proposed underactuated system comprises five joints in closed configuration ($R_1$, $R_2$, $P_1$, $R_3$, $R_4$) creating a five-bar mechanism with two degrees of freedom. A prismatic joint ($P_1$) is actuated by a linear actuator that can concurrently generate torque at the ankle joint ($R_1$) and the toe joint ($R_4$). As described in more detail below, the linear actuator for controlling the prismatic joint $P_1$ is preferably a linear series-elastic actuator.

The ankle torque ratio is defined as the ratio between the force at the input joint ($P_1$) and the torque at the ankle joint ($R_1$), whereas the toe torque ratio is defined as the ratio between the force at the input joint ($P_1$) and the torque at the toe joint ($R_4$). The illustrated actuation mechanism is designed so that the ankle joint torque ratio is larger than the toe torque ratio. In other words, the linear actuator provides greater mechanical advantage with respect to the ankle joint ($R_1$) than the toe joint ($R_4$), such that $\overline{R_1R_2} > \overline{R_3R_4}$. Thus, for a given force provided by the linear actuator at the input joint ($P_1$), the torque at the ankle joint ($R_1$) is greater than the torque at the toe joint ($R_4$).

Figure 1B:
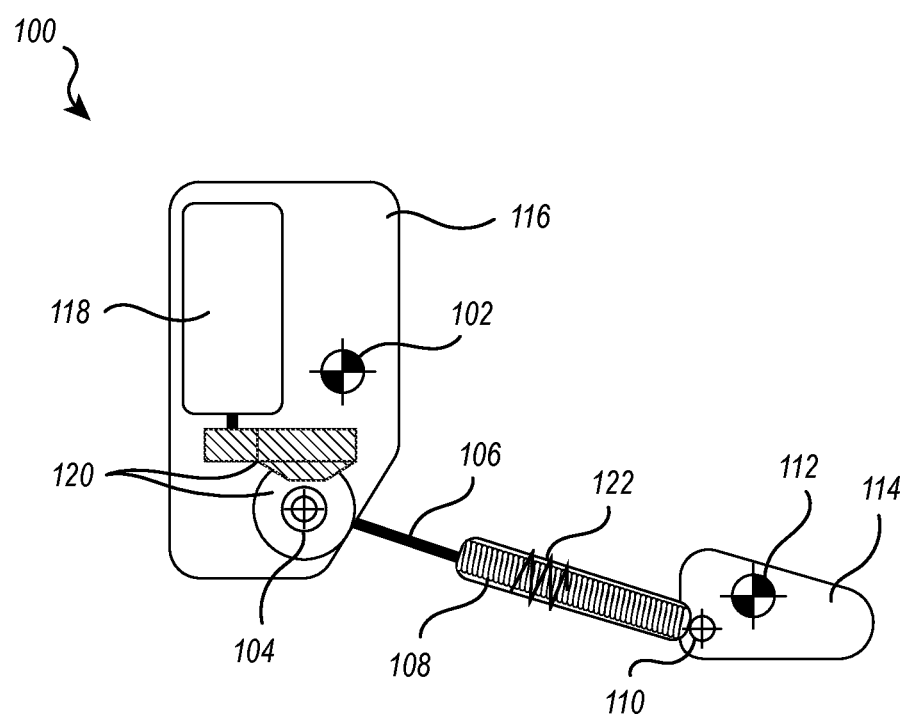
FIG. 1B illustrates a simplified view of a powered ankle-foot prosthetic device incorporating the actuation mechanism of FIG. 1A.

FIG. 1B illustrates a simplified view of a powered ankle-foot prosthetic device 100 incorporating the actuation mechanism of FIG. 1A. The illustrated prosthetic device 100 includes an ankle joint 102 (corresponding to $R_1$), a shank pivot shaft 104 (corresponding to $R_2$), a tarsal assembly 106 that includes or is associated with a linear actuator 108 (corresponding to $P_1$), a toe pivot shaft 110 (corresponding to $R_3$), and a toe joint 112 (corresponding to $R_4$). The prosthetic device 100 also includes a toe assembly 114, a shank assembly 116, a motor 118 attached to or housed within the shank assembly 116, and a power transmission assembly 120 for transmitting power from the motor 118 to the linear actuator 108. In this embodiment, the linear actuator 108 includes a spring 122 to provide a linear series-elastic actuator. Although only a single spring 122 is illustrated, additional springs may be included. Other types of compliant members may additionally or alternatively be included.

In operation, actuation of the linear actuator 108 effectively shortens or lengthens the functional length of the tarsal assembly 106 between the shank pivot shaft 104 and the toe pivot shaft 110. That is, actuation of the linear actuator 108 adjusts the distance between the shank pivot shaft 104 and the toe pivot shaft 110. When this distance is shortened, the movement of the shank pivot shaft 104 relative to the ankle joint 102 causes the ankle to move in plantar flexion. Similarly, upon shortening, movement of the toe pivot shaft 110 relative to the toe joint 112 causes the toe member 114 to move downward in toe flexion. On the other hand, when the distance between the shank pivot shaft 104 and the toe pivot shaft 110 is lengthened, movement of the pivot shaft 104 relative to the ankle joint 102 causes the ankle to move in dorsiflexion, and movement of the toe pivot shaft 110 relative to the toe joint 112 causes the toe member 114 to move upward in toe extension.

A single actuation mechanism therefore effectively controls movement of both the ankle joint and the toe joint. This configuration beneficially provides a compact, relatively simple mechanism for powering both the ankle and toe joints in a prosthesis. As discussed above, prior attempts to incorporate powered ankle and toe joints in a prosthesis have relied on separate actuators for each joint, resulting in a bigger and/or heavier prosthesis.

Figure 3:
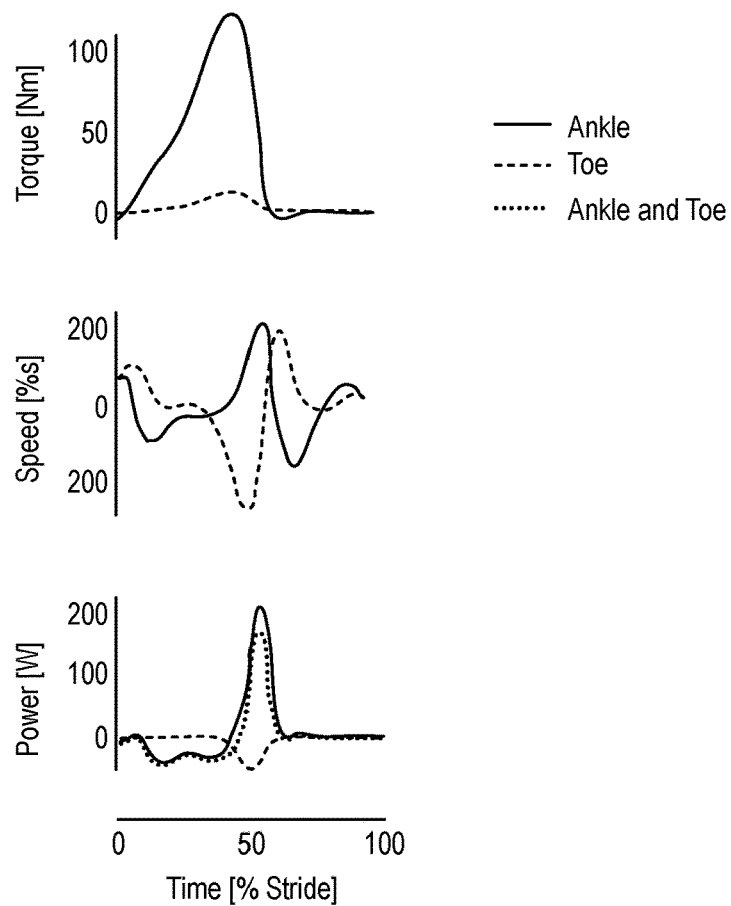
FIG. 3 illustrates biomechanics of the biological ankle and toe.

The disclosed mechanism beneficially aligns with the biomechanics of the biological ankle/foot complex. FIG. 3 shows that during walking, the toe torque is nearly proportional to the ankle torque for large part of the stance phase (20-60% Stride), although the peak torque is much lower for the toe than the ankle (i.e., 0.12 Nm/kg vs 1.35 Nm/kg). Moreover, the velocities of the two joints are comparable in magnitude and opposite in direction, peaking at −218°/s and 280°/s for the ankle and toe joint, respectively. As a result, the toe dissipates power while the ankle generates power.

Thus, during walking, the ankle and toe torque are nearly proportional, and the combined ankle and toe power is smaller than the power of the ankle alone. The present disclosure shows that a single actuator can effectively power both the ankle and toe joint, requiring fewer mechanical and electrical components than using two separate actuators. Moreover, this shows that the combined ankle and toe power requirements are smaller than for the ankle alone. Powering both the ankle and toe joints in a prosthesis is challenging due to the stringent weight and size requirements of such prostheses. The disclosed mechanism addresses these issues by enabling a single actuator to efficiently power both the ankle and the toe joints.

Example Prosthesis Device

Figure 2A:
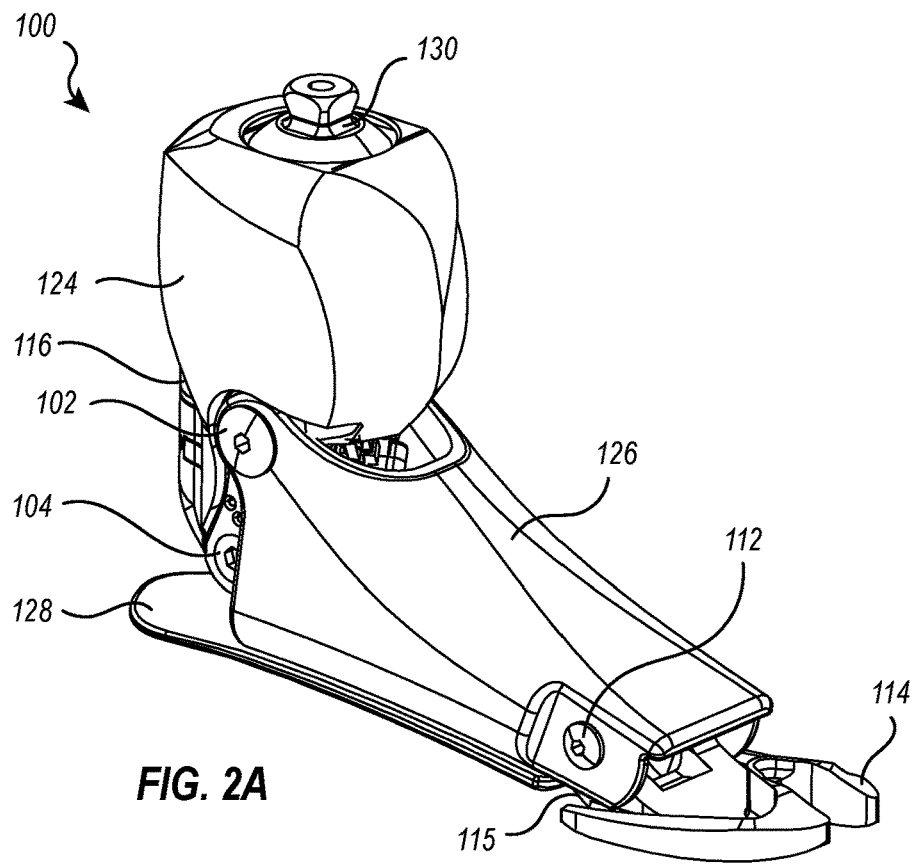
FIGS. 2A-2C show various views of the prosthesis device in greater detail, with FIG. 2A showing the prosthesis device with shell, FIG. 2B showing the prosthesis device with the shell sections removed to better illustrate certain internal components, and FIG. 2C showing a cutaway/sectional view of a distal section of the prosthesis device.
Figure 2B:
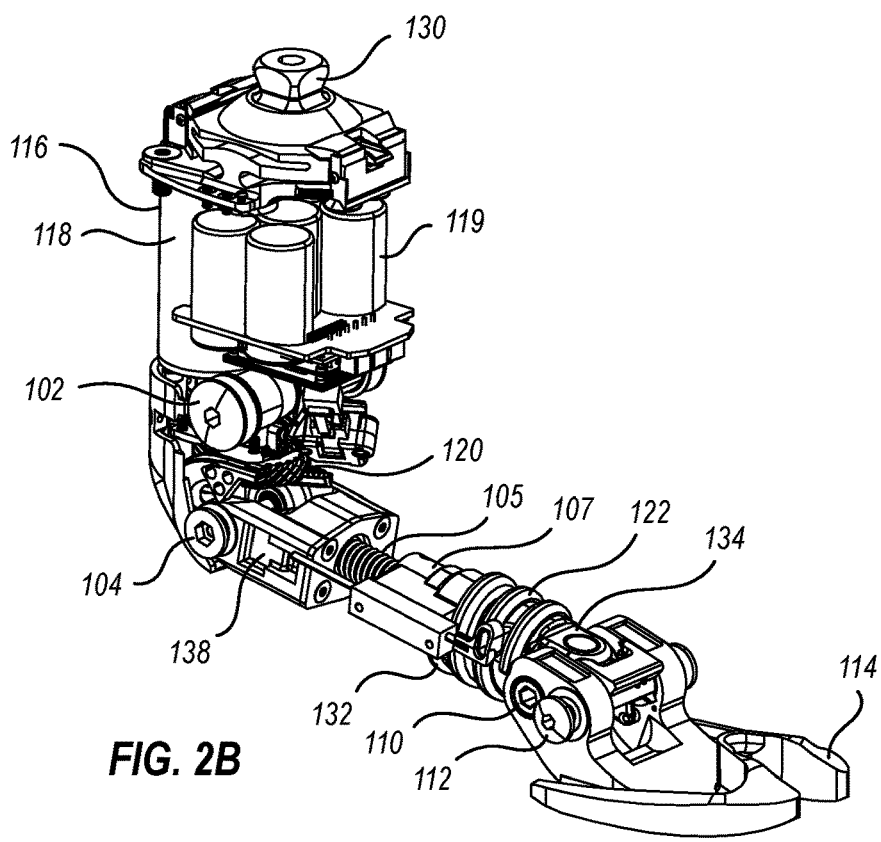
Figure 2C:
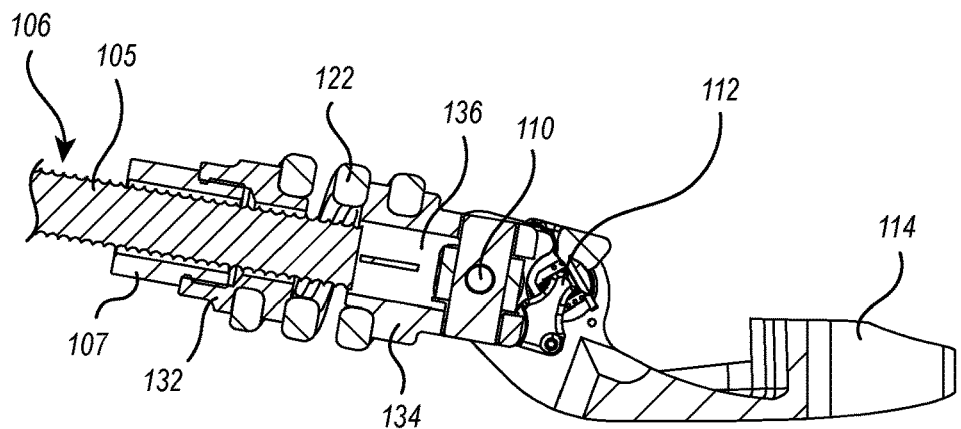

FIGS. 2A-2C show various views of the prosthesis device 100 in greater detail. As shown in FIG. 2A, the prosthesis device 100 includes a shell comprising a shank shell piece 124 and a foot shell piece 126. The prosthesis device 100 also includes a sole 128. The shell 124, 126 may be made from any appropriate material or materials, such as carbon fiber. The shank frame itself may be made from any appropriate material or materials, such as aluminum. The toe assembly 114 may be made from similar materials. Because the motor 118 is in direct contact with the shank frame, the shank frame functions as a heat sink to improve heat dissipation, ultimately allowing for higher motor current and torque without overheating.

A pyramid adaptor 130 is coupled to the shank assembly 116. In some embodiments, the pyramid adaptor 130 includes one or more sensors, such as for sensing ground reaction force. For example, the pyramid adaptor may comprise an instrumented adaptor such as disclosed in United States Patent Application Publication No. 2021/0247249, which is incorporated herein by this reference in its entirety.

FIG. 2A also shows a more detailed example of the foot assembly 114. In some embodiments, the foot assembly 114 includes a mechanical stop 115 that limits the range of motion of the toe joint 112 and prevents it from passing in flexion past the neutral toe joint angle. In this configuration, the kinematic chain loses one degree of freedom, and the actuation mechanism is no longer underactuated, so the ankle joint 102 can be controlled without affecting the toe joint 112.

FIG. 2B illustrates the prosthesis device 100 with the shell sections removed to better illustrate certain internal components. FIG. 2B illustrates the motor 118 and a battery pack 119 housed in the shank assembly 116. The motor 118 is preferably a DC motor (e.g., brushless). However, other embodiments may use any appropriate means of providing power. For example, some embodiments could replace all or a portion of the motor 118 and power transmission assembly 120 with functionally corresponding pneumatic and/or hydraulic components.

In this embodiment, the tarsal assembly 106 comprises a ball screw assembly. Rotation of the screw 105 causes the nut 107 to translate proximally or distally along the length of the screw 105, and this motion effectively shortens or lengthens the screw 105, as described in greater detail below. Toward the proximal end, the screw 105 passes through a bearing assembly 138 and mechanically couples to the power transmission assembly 120. The bearing assembly 138 is coupled to the shank pivot shaft 104. Toward the distal end, the screw 105 passes through the nut 107 and through one or both of anchors 132 and 134. The proximal anchor 132 is mechanically connected to the nut 107 and the distal anchor 134 is mechanically connected to the toe pivot shaft 110.

Other embodiments may utilize alternative types of linear actuators. For example, other embodiments may comprise a leadscrew, screw jack, or roller screw actuator in place of a ball screw actuator. In general, any actuator system capable of providing the disclosed prismatic joint function at the tarsal assembly 106 may be utilized.

The power transmission assembly 120 may be provided in any configuration suitable for transmitting rotational force from the motor 118 to the talus member 106. In a preferred embodiment, the power transmission assembly 120 includes a set of multiple bevel gears. For example, in one embodiment, a first bevel gear is coaxial and directly connected to the output helical gears. A second bevel gear spins freely and is coaxial with the shank pivot shaft 104. A third bevel gear is coaxial to ball screw axis of rotation and transfers power to it. Power may be transferred from the motor 118 to the bevel gears through one or more helical gears, for example.

The illustrated configuration, and those functionally similar to it, enable the motor to remain in a fixed position with the respect to the shank assembly 116. This beneficially impacts the performance and compactness of the prosthesis device 100. For example, because the motor 118 does not pivot with actuation of the ball screw, the space inside the shank assembly 116 and its frame can be more efficiently used. That is, no extra volume is necessary to account for motor movement.

The prosthesis device 100 may be configured with any appropriate range of motion for the ankle and toe joints. Preferably, the ankle joint 102 has a range of motion of at least 30°, or at least 35°, or at least about 40°. For example, the ankle joint 102 may have a range of motion of at least 15°, or at least 17.5°, or at least about 20° in dorsiflexion and at least 15°, or at least 17.5°, or at least about 20° in plantarflexion. Preferably, the toe joint 112 has a range of motion of at least 30°, or at least 35°, or at least 40°, or at least about 45°. For example, the toe joint 112 may have a range of motion of about 45° in toe extension from the neutral position. As discussed elsewhere herein, preferred embodiments prevent the toe joint 112 from moving substantially in toe flexion past the neutral position.

FIG. 2C illustrates a cutaway/sectional view of a distal section of the tarsal assembly 106 and the foot assembly 114. As shown, the spring 122 is connected to and spans between the proximal anchor 132 and distal anchor 134. The proximal anchor 132, spring 122, and distal anchor 134 are configured to allow passage of the screw 105 therethrough. The proximal anchor 132 and distal anchor 134 include bores sized to allow passage of the screw 105 therethrough. The bore of the distal anchor 134 provides a screw space 136 for receiving different proportions of the distal section of the screw 105 depending on the state of the actuator. That is, rotating the screw 105 to pass farther into the screw space 136 shortens the effective length of the screw 105 (i.e., decreases the distance between the shank pivot shaft 104 and the toe pivot shaft 110), whereas rotating the screw 105 to move away from and out of the screw space 136 increases the effective length of the screw 105 (i.e., increases the distance between the shank pivot shaft 104 and the toe pivot shaft 110).

Figure 4A:
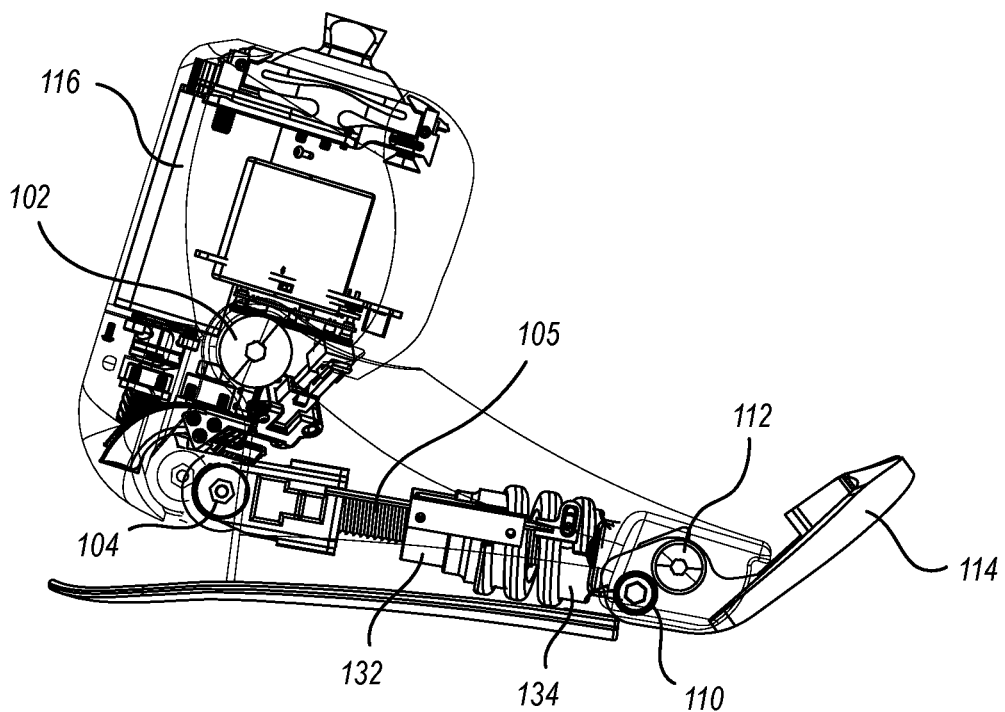
FIG. 4A shows the prosthetic device in a position where the ankle joint is moved in dorsiflexion and the toe joint is moved in toe flexion.

FIG. 4A shows the prosthetic device 100 in a position where the ankle joint 102 is moved in dorsiflexion and the toe joint 112 is moved in toe flexion. For example, the linear actuator may be activated such that rotation of the screw 105 increases the distance between the shank pivot shaft 104 and the toe pivot shaft 110, causing the ankle joint 102 and toe joint 112 to rotate accordingly.

Figure 4B:
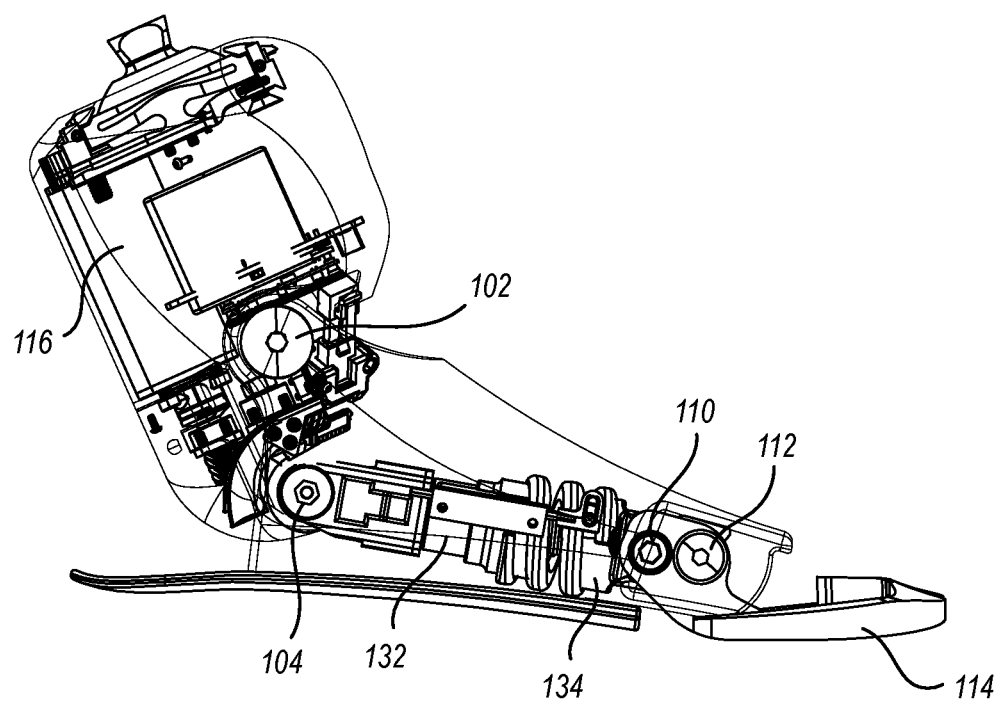
FIG. 4B shows the prosthetic device in a position where the ankle joint is moved in plantarflexion and the toe joint is in the neutral position.

FIG. 4B shows the prosthetic device 100 in a position where the ankle joint 102 is moved in plantarflexion and the toe joint 112 is in the neutral position. For example, the linear actuator may be activated such that rotation of the screw 105 decreases the distance between the shank pivot shaft 104 and the toe pivot shaft 110, causing the ankle joint 102 and toe joint 112 to rotate accordingly.

Figure 5:
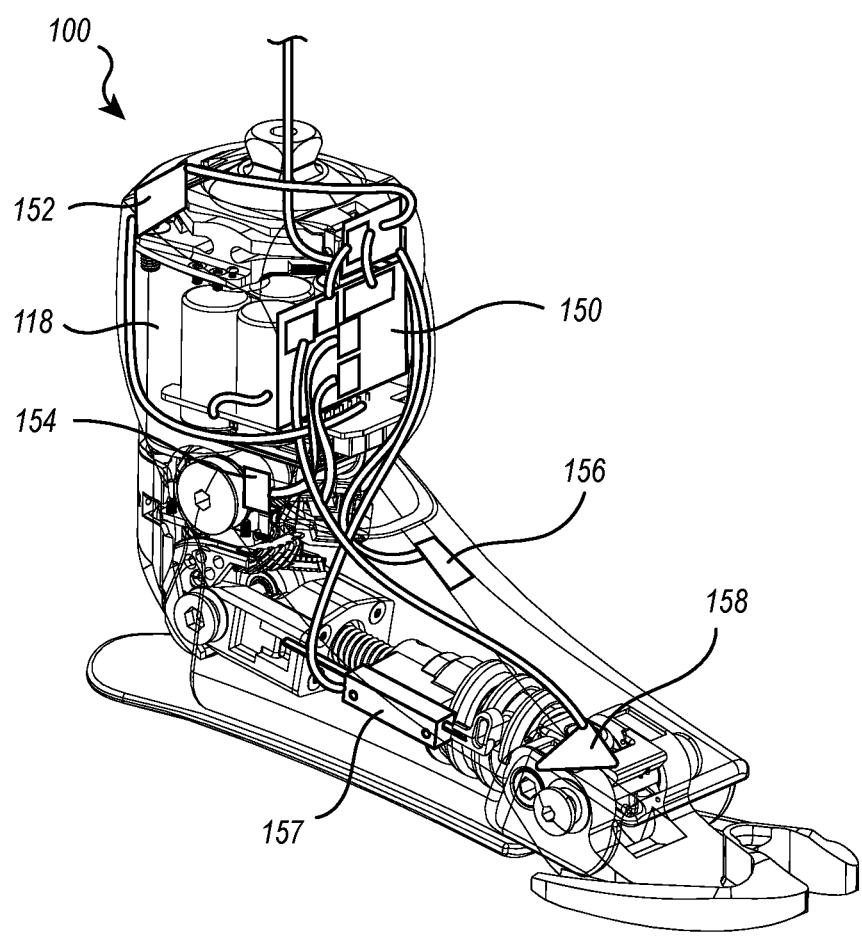
FIG. 5 illustrates various sensors and control elements that may be included in the prosthetic device.

FIG. 5 illustrates various sensors and control elements that may be included in the prosthetic device 100. The illustrated device 100 includes an ankle position sensor 154 and a toe position sensor 158. These may be provided as absolute magnetic encoders, for example. The illustrated device also includes ground force sensor electronics 152 and a spring sensor 157 (e.g., a linear potentiometer). An orientation sensor 156 senses orientation of the device in space. The orientation sensor 156 may include, for example, a 9-axis inertial sensor. Sensor outputs may be directed to a controller 150, which is communicatively coupled to the motor 118. The controller 150 includes one or more processors and may include one or more hardware storage devices (i.e., memory devices) to enable processing of sensor signals and control of the motor.

Performance Examples

Figure 6A:
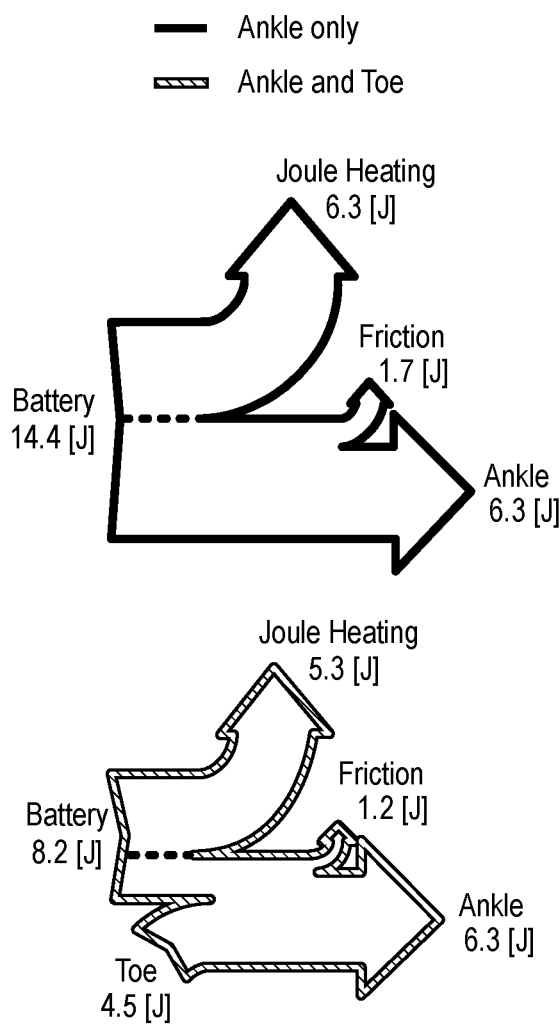
FIG. 6A shows the results of an energy flow analysis comparing the actuation mechanism of the disclosed prosthesis device to an equivalent actuator powering the ankle joint only.
Figure 6B:
FIG. 6B shows battery energy, peak power, and actuator velocity at peak torque of the actuation mechanism of the disclosed prosthesis device compared to the equivalent actuator powering the ankle joint only.
Figure 6B:
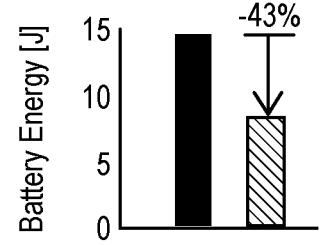
Figure 6B:
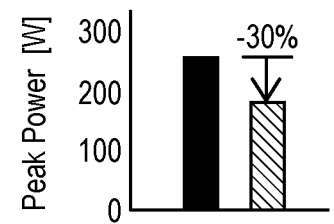
Figure 6B:
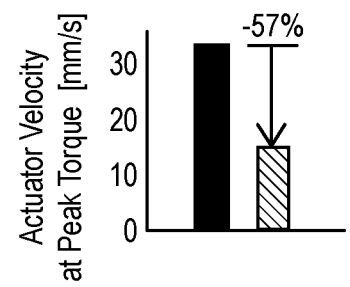

A dynamic simulation compared the performance of the disclosed system to that of an equivalent actuator powering the ankle joint only. The energy flow analysis (FIG. 6A) showed that the ankle-only design requires 14.4 J/stride of electrical energy to produce 6.3 J/stride of mechanical energy at the ankle, achieving an overall efficiency of 43.8%. In comparison, the underactuated design requires 8.2 J/stride of electrical energy, achieving an overall efficiency of 76.8%. Thus, the electrical energy consumption per stride is 43.0% lower in the underactuated design (FIG. 6B).

The energy flow analysis also showed that the reduced electrical energy consumption is primarily due to the toe regenerating 4.5 J/stride of mechanical energy. Finally, the underactuated system showed lower energy losses than the ankle-only design (i.e., −1 J/stride of Joule heating and −0.5 J/stride of friction). These lower energy losses are due to the lower velocity and acceleration of the linear actuator in the underactuated design, which result in lower inertial torque and mechanical power output at the motor (FIG. 6A). Thus, the simulations showed that by leveraging the concurrent torque generation at the toe and ankle joints, a compliant underactuated design can enable a single actuator to power both the ankle and toe joint while reducing electrical energy consumption.

Additional Example Embodiments

The following is a non-exhaustive list of example embodiments provided as numbered items.

1. A powered assistive ankle and foot device, comprising: a shank assembly comprising an ankle joint; a tarsal assembly comprising a proximal section and a distal section, the proximal section being mechanically connected to the shank assembly; a toe assembly mechanically connected to the distal section of the tarsal assembly, the toe assembly comprising a toe joint; and a linear actuator included in or associated with the tarsal assembly, wherein the linear actuator powers movement of both the ankle joint and the toe joint.
2. The device of item 1, wherein: the shank assembly further comprises a shank pivot shaft offset from the ankle joint and mechanically connected to the ankle joint; the proximal section of the tarsal assembly is mechanically connected to the shank pivot shaft; and the toe assembly further comprises a toe pivot shaft offset from the toe joint and mechanically connected to the toe joint, the toe pivot shaft being mechanically connected to the distal section of the tarsal assembly.
3. The device of item 2, wherein the linear actuator is configured to adjust the distance between the shank pivot shaft and the toe pivot shaft to thereby provide simultaneous torque to both the ankle joint and the toe joint.
4. The device of item 2 or item 3, wherein: when a distance between the shank pivot shaft and the toe pivot shaft is lessened, the ankle joint moves in plantarflexion and the toe joint moves in toe flexion; and when a distance between the shank pivot shaft and the toe pivot shaft is increased, the ankle joint moves in dorsiflexion and the toe joint moves in toe extension.
5. The device of any one of items 2-4, wherein an offset distance between the ankle joint and the shank pivot shaft is greater than an offset distance between the toe joint and the toe pivot shaft.
6. The device of any one of items 1-5, wherein the linear actuator comprises a screw assembly including a screw and a nut.
7. The device of item 6, wherein the linear actuator comprises a ball screw assembly.
8. The device of any one of items 1-7, wherein the linear actuator further comprises a compliant element configured to move the toe joint toward a neutral position when no force is applied via the linear actuator.
9. The device of item 8, wherein the compliant element is a spring.
10. The device of item 9 or item 10, wherein the compliant element is mechanically connected to the nut of the screw assembly and functions to move the nut toward a neutral position along the screw when the screw is not rotated.
11. The device of any one of items 8-10, wherein the compliant element is attached to and spans between a proximal anchor and a distal anchor, wherein the proximal anchor is connected to the nut of the screw assembly and the distal anchor is connected to the toe pivot shaft.
12. The device of item 11, wherein the proximal and distal anchors include bores sized to receive the screw.
13. The device of any one of items 1-12, wherein the toe assembly includes a mechanical stop configured to prevent the toe assembly from moving past a neutral position.
14. The device of any one of items 1-13, further comprising a motor mechanically connected to the linear actuator to power the linear actuator.
15. The device of item 14, wherein the motor is attached to or housed within the shank assembly.
16. The device of item 15, wherein the motor does not rotate relative to a shank frame during ankle joint movement of the device.
17. The device of item 16, wherein the motor is in direct contact with the shank frame.
18. The device of any one of items 14-17, wherein the motor is mechanically connected to the linear actuator via a power transmission assembly, wherein the power transmission assembly comprises multiple bevel gears.

19. The device of item 18, wherein the power transmission assembly comprises three bevel gears.

20. The device of item 19, wherein a first bevel gear is coaxial to an output gear, a second bevel gear is coaxial with the shank pivot shaft, and a third bevel gear is coaxial to an axis of rotation of screw of the ball screw assembly and functions to transfer power to the screw.

21. The device of any one of items 1-20, wherein the shank assembly comprises a pyramid adaptor, the pyramid adaptor comprising an integrated ground force sensor.

22. The device of any one of claims 1-21, wherein the device is a prosthesis, orthosis, or exoskeleton component.

The invention claimed is:

1. A powered assistive ankle and foot device, comprising:
a shank assembly comprising an ankle joint and a shank pivot shaft offset from the ankle joint and mechanically connected to the ankle joint;
a tarsal assembly comprising a proximal section and a distal section, the proximal section being mechanically connected to the shank pivot shaft of the shank assembly;
a toe assembly mechanically connected to the distal section of the tarsal assembly, the toe assembly comprising a toe joint and a toe pivot shaft offset from the toe joint and mechanically connected to the toe joint, the toe pivot shaft being mechanically connected to the distal section of the tarsal assembly; and
a linear actuator included in or associated with the tarsal assembly, wherein the linear actuator powers movement of both the ankle joint and the toe joint,
when a distance between the shank pivot shaft and the toe pivot shaft is lessened, the ankle joint moves in plantarflexion and the toe joint moves in toe flexion; and
when a distance between the shank pivot shaft and the toe pivot shaft is increased, the ankle joint moves in dorsiflexion and the toe joint moves in toe extension.

2. The device of claim 1, wherein the linear actuator is configured to adjust the distance between the shank pivot shaft and the toe pivot shaft to thereby provide simultaneous torque to both the ankle joint and the toe joint.

3. The device of claim 1, wherein an offset distance between the ankle joint and the shank pivot shaft is greater than an offset distance between the toe joint and the toe pivot shaft.

4. The device of claim 1, wherein the linear actuator comprises a screw assembly including a screw and a nut.

5. The device of claim 4, wherein the linear actuator comprises a ball screw assembly.

6. The device of claim 4, wherein the linear actuator further comprises a compliant element configured to move the toe joint toward a neutral position when no force is applied via the linear actuator.

7. The device of claim 6, wherein the compliant element is a spring.

8. The device of claim 6, wherein the compliant element is mechanically connected to the nut of the screw assembly and functions to move the nut toward a neutral position along the screw when the screw is not rotated.

9. The device of claim 6, wherein the compliant element is attached to and spans between a proximal anchor and a distal anchor, wherein the proximal anchor is connected to the nut of the screw assembly and the distal anchor is connected to the toe pivot shaft.

10. The device of claim 9, wherein the proximal and distal anchors include bores sized to receive the screw.

11. The device of claim 1, further comprising a motor mechanically connected to the linear actuator to power the linear actuator.

12. The device of claim 11, wherein the motor is attached to or housed within the shank assembly.

13. The device of claim 12, wherein the motor does not rotate relative to a shank frame during ankle joint movement of the device.

14. The device of claim 13, wherein the motor is in direct contact with the shank frame.

15. The device of claim 11, wherein the motor is mechanically connected to the linear actuator via a power transmission assembly, wherein the power transmission assembly comprises multiple bevel gears.

16. The device of claim 15, wherein the power transmission assembly comprises three bevel gears.

17. The device of claim 16, wherein a first bevel gear is coaxial to an output gear, a second bevel gear is coaxial with the shank pivot shaft, and a third bevel gear is coaxial to an axis of rotation of screw of the ball screw assembly and functions to transfer power to the screw.

18. The device of claim 1, wherein the shank assembly comprises a pyramid adaptor, the pyramid adaptor comprising an integrated ground force sensor.

19. The device of claim 1, wherein the device is a prosthesis.

20. A powered assistive ankle and foot device, comprising:
a shank assembly comprising an ankle joint and a shank pivot shaft offset from and mechanically connected to the ankle joint;
a tarsal assembly comprising a proximal section and a distal section, the proximal section being mechanically connected to the shank pivot shaft;
a toe assembly comprising a toe joint and a toe pivot shaft offset from and mechanically connected to the toe joint, the toe pivot shaft being mechanically connected to the distal section of the tarsal assembly; and
a linear actuator associated with the tarsal assembly, the linear actuator being configured as linear series elastic actuator comprising a screw assembly and a spring,
wherein an offset distance between the ankle joint and the shank pivot shaft is greater than an offset distance between the toe joint and the toe pivot shaft, and
wherein the linear actuator is configured to adjust the distance between the shank pivot shaft and the toe pivot shaft to thereby provide simultaneous torque to both the ankle joint and the toe joint.

21. The device of claim 20, wherein the spring is mechanically connected to a nut of the screw assembly and functions to move the nut toward a neutral position along a screw of the screw assembly when the screw is not rotated.

22. The device of claim 21, wherein the spring is attached to and spans between a proximal anchor and a distal anchor, wherein the proximal anchor is connected to the nut of the screw assembly and the distal anchor is connected to the toe pivot shaft, and wherein proximal and distal anchors include bores sized to receive the screw.

23. The device of claim 21, further comprising a motor mechanically connected to the linear actuator to power the linear actuator, wherein the motor is attached to or housed within the shank assembly, and wherein the motor does not rotate relative to a shank frame during ankle joint movement of the device.

24. The device of claim 21, wherein the device is a prosthesis.

25. A powered assistive ankle and foot device, comprising:
- a shank assembly comprising an ankle joint;
- a tarsal assembly comprising a proximal section and a distal section, the proximal section being mechanically connected to the shank assembly;
- a toe assembly mechanically connected to the distal section of the tarsal assembly, the toe assembly comprising a toe joint; and
- a linear actuator included in or associated with the tarsal assembly, wherein the linear actuator powers movement of both the ankle joint and the toe joint, wherein the linear actuator comprises a screw assembly including a screw and a nut, and comprises a compliant element configured to move the toe joint toward a neutral position when no force is applied via the linear actuator
- wherein the compliant element is mechanically connected to the nut of the screw assembly and functions to move the nut toward a neutral position along the screw when the screw is not rotated.

26. The device of claim 25, further comprising a motor mechanically connected to the linear actuator to power the linear actuator, wherein the motor is attached to or housed within the shank assembly, and wherein the motor does not rotate relative to a shank frame during ankle joint movement of the device.

27. The device of claim 25, further comprising a motor mechanically connected to the linear actuator to power the linear actuator, wherein the motor is mechanically connected to the linear actuator via a power transmission assembly, wherein the power transmission assembly comprises multiple bevel gears.

28. A powered assistive ankle and foot device, comprising:
- a shank assembly comprising an ankle joint;
- a tarsal assembly comprising a proximal section and a distal section, the proximal section being mechanically connected to the shank assembly;
- a toe assembly mechanically connected to the distal section of the tarsal assembly, the toe assembly comprising a toe joint; and
- a linear actuator included in or associated with the tarsal assembly, wherein the linear actuator powers movement of both the ankle joint and the toe joint, wherein the linear actuator comprises a screw assembly including a screw and a nut, and comprises a compliant element configured to move the toe joint toward a neutral position when no force is applied via the linear actuator,
- wherein the compliant element is attached to and spans between a proximal anchor and a distal anchor, wherein the proximal anchor is connected to the nut of the screw assembly and the distal anchor is connected to the toe pivot shaft.

29. The device of claim 28, wherein the proximal and distal anchors include bores sized to receive the screw.

30. The device of claim 28, further comprising a motor mechanically connected to the linear actuator to power the linear actuator, wherein the motor is attached to or housed within the shank assembly, and wherein the motor does not rotate relative to a shank frame during ankle joint movement of the device.

31. The device of claim 28, further comprising a motor mechanically connected to the linear actuator to power the linear actuator, wherein the motor is mechanically connected to the linear actuator via a power transmission assembly, wherein the power transmission assembly comprises multiple bevel gears.

32. A powered assistive ankle and foot device, comprising:
- a shank assembly comprising an ankle joint;
- a tarsal assembly comprising a proximal section and a distal section, the proximal section being mechanically connected to the shank assembly;
- a toe assembly mechanically connected to the distal section of the tarsal assembly, the toe assembly comprising a toe joint;
- a linear actuator included in or associated with the tarsal assembly, wherein the linear actuator powers movement of both the ankle joint and the toe joint; and
- a motor mechanically connected to the linear actuator to power the linear actuator,
- wherein the motor is attached to or housed within the shank assembly and wherein the motor does not rotate relative to a shank frame during ankle joint movement of the device.

33. The device of claim 32, wherein the motor is in direct contact with the shank frame.

34. A powered assistive ankle and foot device, comprising:
- a shank assembly comprising an ankle joint;
- a tarsal assembly comprising a proximal section and a distal section, the proximal section being mechanically connected to the shank assembly;
- a toe assembly mechanically connected to the distal section of the tarsal assembly, the toe assembly comprising a toe joint;
- a linear actuator included in or associated with the tarsal assembly, wherein the linear actuator powers movement of both the ankle joint and the toe joint; and
- a motor mechanically connected to the linear actuator to power the linear actuator,
- wherein the motor is mechanically connected to the linear actuator via a power transmission assembly, wherein the power transmission assembly comprises multiple bevel gears.

35. The device of claim 34, wherein the power transmission assembly comprises three bevel gears.

36. The device of claim 35, wherein a first bevel gear is coaxial to an output gear, a second bevel gear is coaxial with the shank pivot shaft, and a third bevel gear is coaxial to an axis of rotation of screw of the ball screw assembly and functions to transfer power to the screw.

* * * * *